United States Patent
Kovoor et al.

(10) Patent No.: US 11,517,264 B2
(45) Date of Patent: Dec. 6, 2022

(54) METHODS AND APPARATUSES FOR MONITORING CARDIAC DYSFUNCTION

(71) Applicant: Western Sydney Local Health District, New South Wales (AU)

(72) Inventors: Pramesh Kovoor, New South Wales (AU); Jim Pouliopoulos, New South Wales (AU); Tony Barry, New South Wales (AU)

(73) Assignee: Western Sydney Local Health District, New South Wales (AU)

( * ) Notice: Subject to any disclaimer, the term of this patent is extended or adjusted under 35 U.S.C. 154(b) by 343 days.

(21) Appl. No.: 16/483,535

(22) PCT Filed: Feb. 6, 2018

(86) PCT No.: PCT/AU2018/050079
§ 371 (c)(1),
(2) Date: Aug. 5, 2019

(87) PCT Pub. No.: WO2018/141028
PCT Pub. Date: Aug. 9, 2018

(65) Prior Publication Data
US 2020/0129126 A1   Apr. 30, 2020

(30) Foreign Application Priority Data

Feb. 6, 2017   (AU) ................................ 2017900356

(51) Int. Cl.
*A61B 5/0215* (2006.01)
*A61B 5/00* (2006.01)
(Continued)

(52) U.S. Cl.
CPC .......... *A61B 5/6869* (2013.01); *A61B 5/0215* (2013.01); *A61B 5/0245* (2013.01);
(Continued)

(58) Field of Classification Search
CPC . A61B 5/02007; A61B 5/6869; A61B 5/0245; A61B 5/11; A61B 5/0031;
(Continued)

(56) References Cited

U.S. PATENT DOCUMENTS 6,002,955 A   12/1999 Willems et al.
6,077,236 A   6/2000 Cunningham
(Continued)

FOREIGN PATENT DOCUMENTS

JP   H11-401 A   1/1999
JP   2006-518631 A   8/2006
(Continued)

OTHER PUBLICATIONS

M. Booner, et al., "Early Performance and Safety of the Micra Transcatheter Pacemaker in Pigs," Pacing and Clinical Electrophysiology published by Wiley Periodicals, Inc., Nov. 2015, vol. 38, pp. 1248-1259.

(Continued)

*Primary Examiner* — Deborah L Malamud
(74) *Attorney, Agent, or Firm* — Morgan, Lewis & Bockius LLP

(57) ABSTRACT

A method of monitoring cardiac dysfunction, such as pericardial effusion, is disclosed. The method uses an indwelling probe inserted within a coronary sinus or a chamber or vessel of the heart, the probe having motion sensing means configured to sense motion of the probe based on movement of the wall of the coronary sinus or other chamber or vessel. Data is obtained from the motion sensing means and processed to monitor for cardiac dysfunction. The monitoring can be in real-time and can utilise one or more three-axis accelerometers. In some embodiments, two or more three- (Continued)

axis accelerometers are spaced longitudinally along an elongate body of the probe, which can increase accuracy and reliability of monitoring.

18 Claims, 10 Drawing Sheets

(51) Int. Cl.
*A61B 5/0245* (2006.01)
*A61B 5/11* (2006.01)

(52) U.S. Cl.
CPC ..... *A61B 5/1107* (2013.01); *A61B 2562/0219* (2013.01); *A61B 2562/043* (2013.01)

(58) Field of Classification Search
CPC ... A61B 5/1102; A61B 5/1107; A61B 5/0215; A61N 1/0587; A61N 1/3627; A61N 1/36514; A61N 1/46; A61N 2001/0585; A61N 1/36578
See application file for complete search history.

(56) References Cited

U.S. PATENT DOCUMENTS

| | | | |
|---|---|---|---|
| 6,923,772 B2 | 8/2005 | Yu et al. | |
| 6,980,866 B2 | 12/2005 | Yu et al. | |
| 7,130,681 B2 | 10/2006 | Gebhardt et al. | |
| 7,139,608 B2 | 11/2006 | Ideker et al. | |
| 7,445,605 B2 | 11/2008 | Overall et al. | |
| 7,653,437 B2 | 1/2010 | Prakash et al. | |
| 7,729,783 B2 | 6/2010 | Michels et al. | |
| 8,032,206 B1 | 10/2011 | Farazi et al. | |
| 2002/0045809 A1 | 4/2002 | Ben-Haim | |
| 2004/0022640 A1 | 2/2004 | Siess et al. | |
| 2006/0095085 A1 | 5/2006 | Marcus et al. | |
| 2006/0161211 A1 | 7/2006 | Thompson et al. | |
| 2006/0178586 A1 | 8/2006 | Dobak, III | |
| 2010/0114230 A1 | 5/2010 | Audit et al. | |
| 2011/0054290 A1 | 3/2011 | Derchak | |
| 2011/0098771 A1 | 4/2011 | Thakur et al. | |
| 2012/0212380 A1 | 8/2012 | Theobold et al. | |
| 2014/0275957 A1 | 9/2014 | Lupotti | |
| 2015/0164322 A1 | 1/2015 | Derchak | |

FOREIGN PATENT DOCUMENTS

| | | |
|---|---|---|
| JP | 2007-503280 A | 2/2007 |
| JP | 2007-222644 A | 9/2007 |
| JP | 2011-104352 A | 6/2011 |
| WO | 1995/03086 A2 | 2/1995 |
| WO | 2004/066825 A3 | 8/2004 |
| WO | 2004/101066 A1 | 11/2004 |
| WO | 2008/076464 A2 | 6/2008 |
| WO | 2013121431 A1 | 8/2013 |

OTHER PUBLICATIONS

Ole-Johannes H.N. Grymyr, et al., "Continuous monitoring of cardiac function by 3-dimensional accelerometers in a closed-chest pig model," Interactive Cardiovascular and Thoracic Surgery, vol. 21, 2015, pp. 573-582.

Written Opinion and International Search Report dated Mar. 7, 2018 issued in International Patent Application No. PCT/AU2018/050079.

Japanese Office Action dated Nov. 24, 2021 issued in Japanese Patent Application No. 2019-542445 (with English translation).

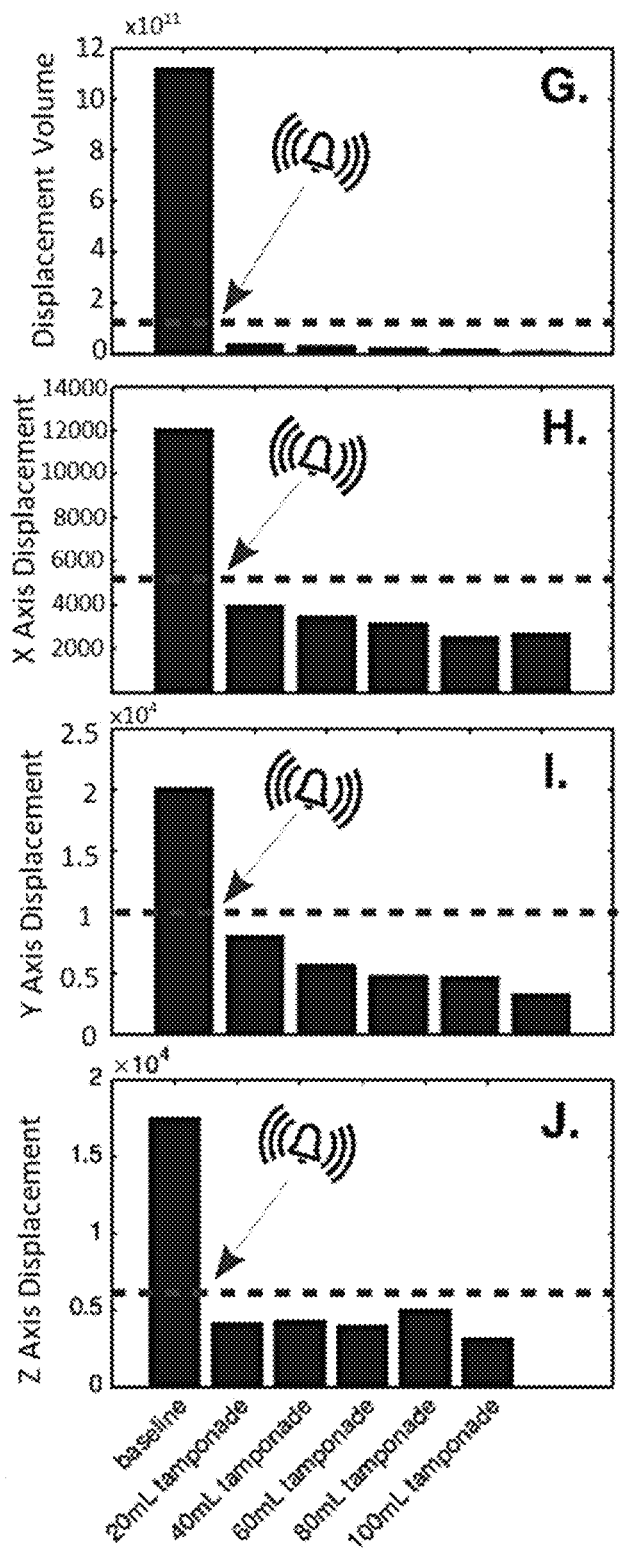
Figure 10 (Contd.)

METHODS AND APPARATUSES FOR MONITORING CARDIAC DYSFUNCTION

CROSS-REFERENCE TO RELATED APPLICATION

The present application claims priority to Australian provisional application no. 2017900356, filed on 6 Feb. 2017, the entire content of which is herein incorporated by reference.

TECHNICAL FIELD

The present invention relates to methods and apparatuses for monitoring cardiac dysfunction such as irregularities in cardiac wall motion.

BACKGROUND

Monitoring of cardiac wall motion is important in many clinical cardiac procedures. As the number and complexity of percutaneous intracardiac procedures continues to increase and a variety of new technologies for structural heart disease and electrophysiology interventions are introduced, the risk of periprocedural injury to the heart also increases. Many of these procedures have in common the need for intraprocedural anticoagulation and a number require transseptal puncture to access the heart.

Percutaneous based catheterisation is the most rapidly growing technique in the field of interventional cardiology for diagnosing and treating diseases in the heart. Perforation or full-thickness injury of the heart wall during catheterisation procedures occurs at a rate of approximately 1 to 6% clinically depending on the aetiology and complexity of the procedure. This often leads to pericardial effusion, which involves the ejection of blood or fluid from within the perforated (or injured) cardiac chamber into the pericardial space, and more seriously cardiac tamponade, which is the crushing of the heart due to an accumulation of blood or fluid in the pericardial space, thus preventing the heart from beating. Both conditions lead to a loss of contractile function of the heart wall.

Monitoring cardiac function is also desirable for coronary intervention procedures. Coronary intervention is a procedure which aims to restore blood flow to an occluded artery of the heart via intravascular deployment of a balloon designed to distend the artery or deploy a stent. The act of ballooning in coronary interventions temporarily causes cardiac ischemia (lack of oxygen due to interrupted coronary blood flow). This may lead to impaired cardiac function, such as loss of contractility of the heart wall, and could contribute to sudden cardiac death.

Monitoring cardiac function may also be desirable for cardiac ablation procedures. It is well recognised that blood volume pressure of the heart may increase due to the overload of physiological normal saline (irrigation) during cardiac ablation procedures. The increased blood volume pressure can have adverse effects on cardiac wall motion, leading to complications during the procedure.

In the electrophysiology setting, an increased risk of pericardial effusion may be associated with intracardiac or epicardial arrhythmia ablations of any chamber of the heart, placement of biventricular pacemakers, and implantable cardioverter-defibrillators.

Implantable cardioverter-defibrillators (ICDs) or pacemakers are often implanted in patients at risk of cardiac arrhythmias or to enable cardiac rate control (pacing) in patients with cardiac dysfunction. The modality of treatment by such devices is achieved by electrical stimulation of the heart muscle via an electrode imbedded within the heart wall. Under certain situations, cardiac electrical stimulation by such devices may be ineffective when physiological changes to the heart occur, such as ischemia or heart failure, which may result in loss of contractile function of the heart wall and may lead to potentially life threatening circumstances. As such, effective delivery of therapy from ICDs or pacemakers depends upon accurate measurement of intrinsic cardiac activity.

Current methods used to monitor cardiac activity, particularly pericardial effusion and cardiac tamponade, involve hemodynamic monitoring (blood pressure measurement), echocardiographic assessment, and fluoroscopic assessment. Hemodynamic assessment, which is often performed continuously in cardiac procedures, has low sensitivity to early changes in cardiac contractility. Current imaging modalities involving x-ray and ultrasound are also limited as they are often utilised reactively to hemodynamic compromise and not proactively.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

An aspect of the present disclosure provides a method of monitoring cardiac dysfunction using an indwelling probe inserted within the coronary sinus of a patient, the probe having motion sensing means configured to sense motion of the probe based on movement of the wall of the coronary sinus, the method comprising:

obtaining data from the motion sensing means and processing said data to monitor for cardiac dysfunction.

Another aspect of the present disclosure provides an apparatus comprising:

an indwelling probe comprising:
an elongate body adapted for insertion within a coronary sinus of a patient; and
motion sensing means coupled to the elongate body and configured to sense motion of the probe based on movement of the wall of the coronary sinus; and
a processor coupled to the probe for receiving data obtained from the motion sensing means and processing said data to monitor for cardiac dysfunction.

The indwelling probe may have a diameter ranging from 5 to 8 Fr (1.7 to 2.7 mm) or otherwise. The indwelling probe may have a length ranging from 65 cm to 115 cm or otherwise.

The data from the motion sensing means may comprise acceleration data, indicative of acceleration and/or deceleration of the wall.

The method and apparatus may comprise:
recording acceleration data from the motion sensing means;
deriving displacement data from the acceleration data; and
comparing the displacement data with baseline data.

In yet a further aspect of the present disclosure, there is provided a method of monitoring cardiac dysfunction using an indwelling probe inserted within a heart vessel, the probe having motion sensing means configured to sense motion of the probe, the method comprising:

recording acceleration data from the motion sensing means based on movement of the wall of the heart vessel;

deriving displacement data from the acceleration data; and comparing the displacement data with baseline data to monitor for cardiac dysfunction.

Another aspect of the present invention provides an apparatus comprising:

an indwelling probe comprising:
  an elongate body adapted for insertion within a heart vessel; and
  motion sensing means coupled to the elongate body and configured to sense motion of the probe based on movement of the wall of the heart vessel; and
a processor coupled to the probe for receiving data obtained from the motion sensing means and processing said data to monitor for cardiac dysfunction.

A further aspect of the present invention provides an apparatus comprising:

an indwelling probe comprising:
  an elongate body adapted for insertion within a chamber of the heart; and
  motion sensing means coupled to the elongate body and configured to sense motion of the probe based on movement of the wall of the chamber of the heart; and
a processor coupled to the probe for receiving data obtained from the motion sensing means and processing said data to monitor for cardiac dysfunction.

In any of the above methods, the processor may form part of a computer system and/or the processing steps may be conducted at least partially using a computer system. The computer system may comprise a computer device with a processor and memory.

The motion sensing means may comprise a three-axis accelerometer located at or adjacent a distal end of the elongate body. Acceleration data recorded from the three-axis accelerometer may be filtered to remove signal artefact arising from, for example, respiration movement, cardiac ectopy or patient movement. The probe may be provided at least in part by a catheter that includes the elongate body.

Deriving displacement data may comprise performing a first calculation to determine first displacement data from the acceleration data and performing a second calculation to determine volumetric displacement data of the probe from the first displacement data. Comparing the displacement data with baseline data may comprise comparing volumetric displacement data determined from the second calculation with baseline data.

At least one electrode may be disposed on the external surface of the elongate body. In some embodiments, two or more electrodes may be spaced longitudinally along the elongate body. The electrode(s) may be configured to detect electrograms from cardiac activity. In some embodiments, the same or additional electrodes may be configured to deliver electrical current for stimulation of the heart. Electrograms detected from the electrode(s) may be recorded and may, in addition, be used to calculate beat-to-beat cardiac cycle timing data. The beat-to-beat cardiac cycle timing data may then be used to correct the first displacement data to account for displacement drift of the probe. The second calculation to determine volumetric displacement data of the probe may be based on the corrected first displacement data, for example.

One or more sensors may be coupled to the processor. The sensor(s) may be configured to provide additional reference data, such as external reference data. The sensor(s) may comprise skin surface electrode(s), temperature sensor(s) (e.g., thermocouples or thermistors), ultrasound probe, radiofrequency patch, magnetometer or induction coil, x-ray fluoroscopy apparatus, and/or three-dimensional electroanatomical mapping system. The additional reference data may comprise electrocardiograms, echocardiograms, bio-impedance data, magnetic field information or induction coil data, x-ray fluoroscopy data, catheter positioning information, temperature information and/or anatomical structure depending on the sensor(s) used.

In some embodiments, electrocardiograms from the skin surface electrode(s) may be recorded and may, in addition, be used to calculate beat-to-beat cardiac cycle timing data. Again, the beat-to-beat cardiac cycle timing data may then be used to correct the first displacement data to account for displacement drift of the probe. The second calculation to determine volumetric displacement data of the probe may be based on the corrected first displacement data, for example. Alternatively, or additionally, the additional reference data may be used to correct the acceleration data to account for positional mis-orientation of the probe, filter the acceleration data to remove signal artefact, and/or provide additional diagnostic information regarding cardiac function. Once again, the second calculation to determine volumetric displacement data of the probe may be based on the corrected first displacement data.

In some embodiments, a single three-axis accelerometer may be provided. Alternatively, two or more three-axis accelerometers may be provided that may be spaced longitudinally along the elongate body. Deriving volumetric displacement data may comprise performing a first calculation to determine first displacement data from the acceleration data, cross-validating the first displacement data to differentiate artefact motion data from validated displacement data, and performing a second calculation to determine volumetric displacement data of the probe from the validated displacement data. Additionally, or alternatively, cardiac wall deformation data, assessed as the displacement deviations that may arise between accelerometer pairs, may be calculated based on the validated displacement data.

In any of the above aspects and embodiments, one or more alerts may be generated when the volumetric displacement data and/or the cardiac wall deformation data changes significantly from baseline data.

A further aspect of the present invention provides a method comprising:

inserting an indwelling probe within a coronary sinus of a patient, the probe having motion sensing means configured to sense motion of the probe based on movement of the wall of the coronary sinus; and coupling the probe to a processor, the processor being configured to receive and process acceleration data obtained from the motion sensing means to monitor for cardiac dysfunction.

In one embodiment, a distal end of the probe may be located adjacent to the valve of Vieussens of the coronary sinus, for example.

The motion sensing means may comprise a three-axis accelerometer located adjacent the distal end of the probe such that, when the indwelling probe is positioned for use, the accelerometer is positioned within the distal aspect of the coronary sinus in approximation to the postero-lateral to lateral aspect of the atrioventricular groove of the heart.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Preferred embodiments of the invention will be described hereinafter, by way of examples only, with reference to the accompanying drawings, in which.

DESCRIPTION OF EMBODIMENTS

Figure 1:
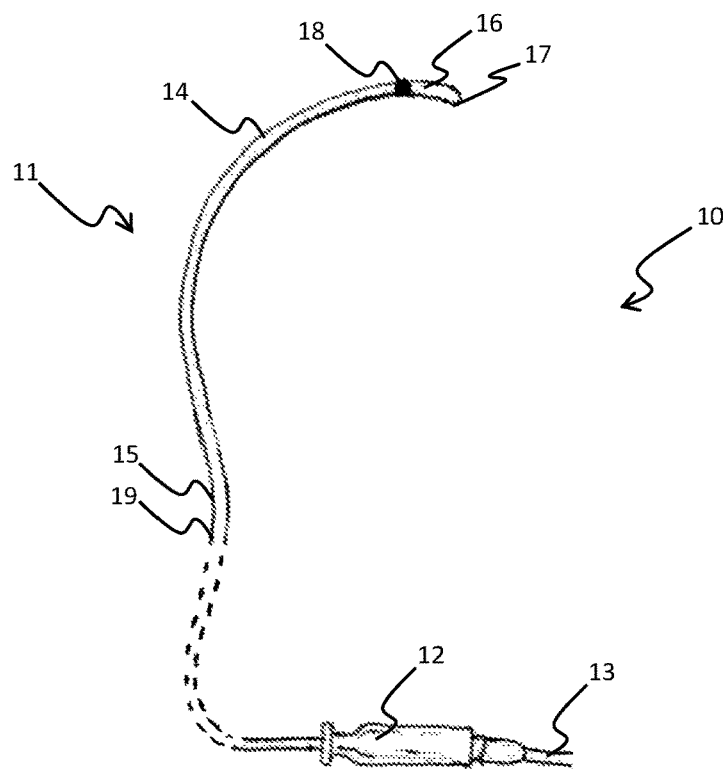
FIG. 1 is a top view of components of an apparatus according to an embodiment of the present disclosure.

FIG. 1 shows an apparatus 10 according to a first embodiment of the present disclosure. The apparatus 10 comprises an indwelling probe 11 connected to a processor (not shown in FIG. 1) via a handle 12 and a lead 13.

The indwelling probe 11 has an elongate body 14 that is adapted to be inserted within a heart vessel of a patient. In this particular embodiment, the heart vessel is a coronary sinus (not shown). The elongate body 14 has a proximal end 15, a distal end 16 and a distal tip 17. The indwelling probe 11 also includes a shank 19 that connects the proximal end 15 of the elongate body 14 to the handle 12. In this embodiment, the indwelling probe 11 has a diameter ranging from 5 to 8 Fr (1.7 to 2.7 mm) and a length ranging from 65 cm to 115 cm, making it particularly suitable for insertion in the coronary sinus in accordance with methods described herein. Nevertheless, it is to be understood that the diameter and length of the indwelling probe may vary depending on the manner of surgical insertion (i.e. radial approach or femoral approach) and/or the anatomy of the patient.

The indwelling probe 11 also includes motion sensing means coupled to the elongate body 14. The motion sensing means is configured to sense motion of the indwelling probe 11 based on movement of the wall of the coronary sinus. In some embodiments, the motion sensing means comprises at least one three-axis accelerometer. In the embodiment depicted in FIG. 1, the motion sensing means comprises a single three-axis accelerometer 18, also referred to hereinafter as a "distal accelerometer" 18. In some embodiments, the distal accelerometer 18 may be located at or adjacent the distal tip 17. In the embodiment depicted in FIG. 1, the distal accelerometer 18 is located approximately 2 cm from the distal tip 17 although in alternative embodiments it may be located anywhere between 0 cm and 10 cm, 0.5 cm and 8 cm, 1 cm and 6 cm or 1 cm and 4 cm, from the distal tip 17 or otherwise.

Figure 2:
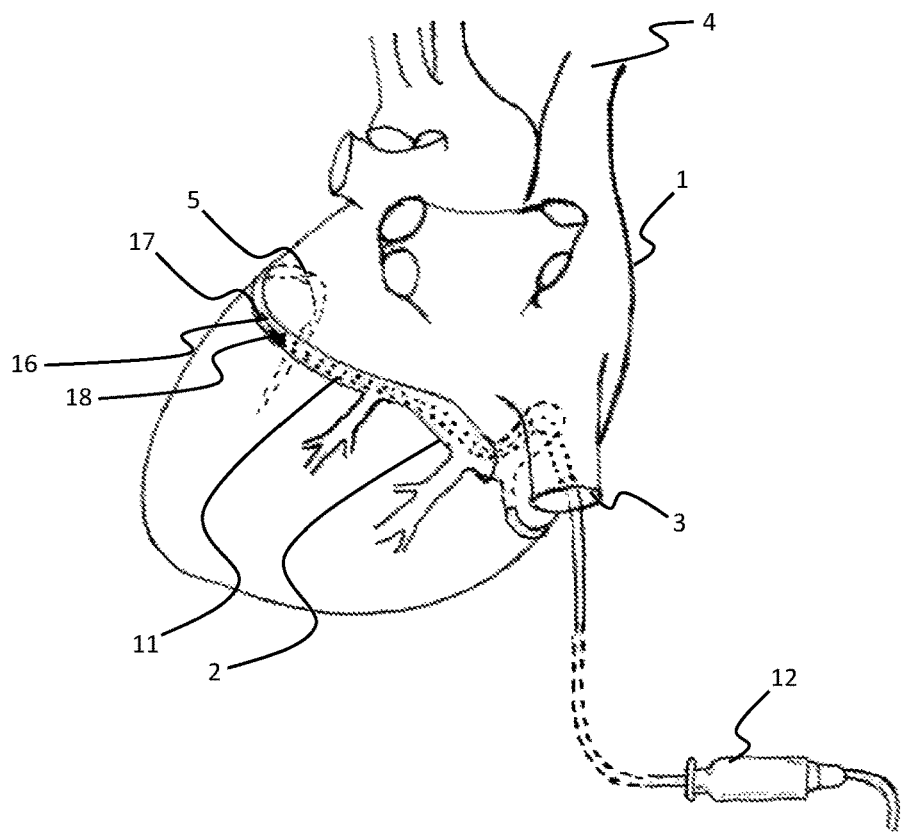
FIG. 2 is a posterolateral view of a heart with an indwelling probe of the apparatus of FIG. 1, positioned for use.

An example method of positioning the indwelling probe 11 in the coronary sinus 2 of a heart 1 according to the present disclosure will now be described with reference to FIG. 2. It is known that the coronary sinus 2 runs along an atrioventricular groove of the heart 1. The indwelling probe 11 is inserted within the coronary sinus 2, distal tip 17 first, via the inferior vena cava 3 of the heart 1. In alternative embodiments, the indwelling probe 11 may be inserted within the coronary sinus 2 via the superior vena cava 4 of the heart 1. When positioned for use, the distal end 16 of the indwelling probe 11 is located adjacent the valve of Vieussens 5 of the coronary sinus 2 and the distal accelerometer 18 is located in proximity to the postero-lateral to lateral aspect of the atrioventricular groove. The present disclosure recognises that cardiac wall motion during a cardiac cycle is greater at the lateral aspect of the atrioventricular groove than the proximal aspect of the coronary sinus (coronary ostium). Having the distal accelerometer 18 at or adjacent the distal tip 17, such that the distal accelerometer is positioned in proximity to the postero-lateral to lateral aspect of the atrioventricular groove, can allow for ease of measurement and greater sensitivity to changes in cardiac wall motion.

The proximal end 15 of the indwelling probe 11 is then coupled to the processor. However, it will be appreciated that, in alternative embodiments, the indwelling probe 11 may be coupled to the processor prior to insertion of the indwelling probe 11 within the coronary sinus 2.

Figure 3:
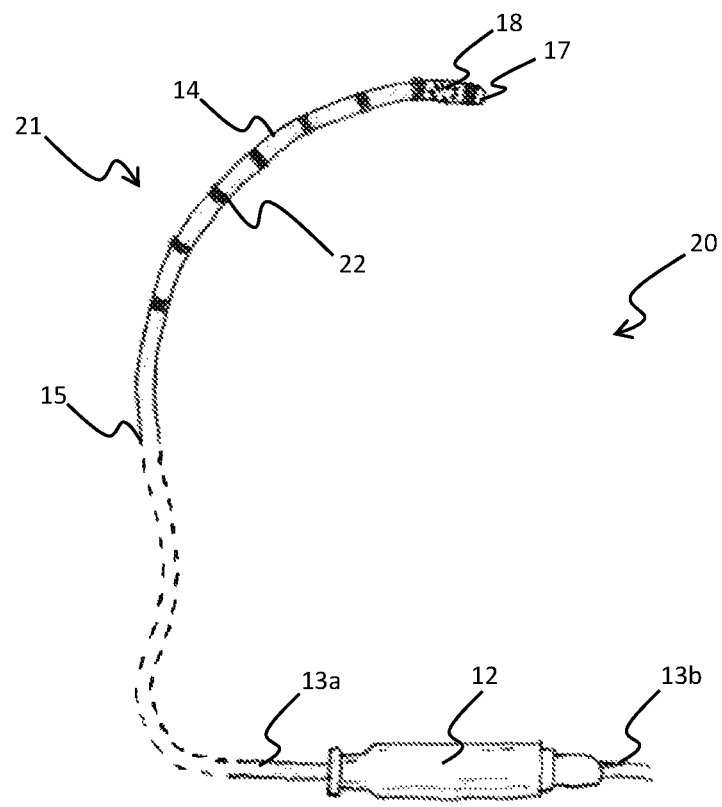
FIG. 3 is a top view of components of an apparatus according to another embodiment of the present disclosure.

FIG. 3 shows another embodiment of an apparatus 20 similar to that shown in FIG. 1, and like features have been indicated with like reference numerals. In the apparatus 20, indwelling probe 21 further comprises at least one electrode disposed on the external surface of the elongate body. The at least one electrode is configured to detect electrograms from cardiac activity. In some embodiments, the indwelling probe 21 comprises two or more of the electrodes spaced longitudinally along the elongate body 14. In some embodiments, the indwelling probe comprises four to ten of the electrodes. In the embodiment depicted in FIG. 3, eight of the electrodes 22 are spaced longitudinally along the elongate body 14 between the distal tip 17 and the proximal end 15. In some embodiments, the electrodes 22 are evenly spaced at a distance of approximately 5 mm. In other embodiments, the electrodes 22 are unevenly spaced at distances of between approximately 2 mm and 5 mm. The indwelling probe 21 of FIG. 3 is positioned for use in the same manner as that discussed above with respect to the indwelling probe 11 of FIG. 1.

Figure 4:
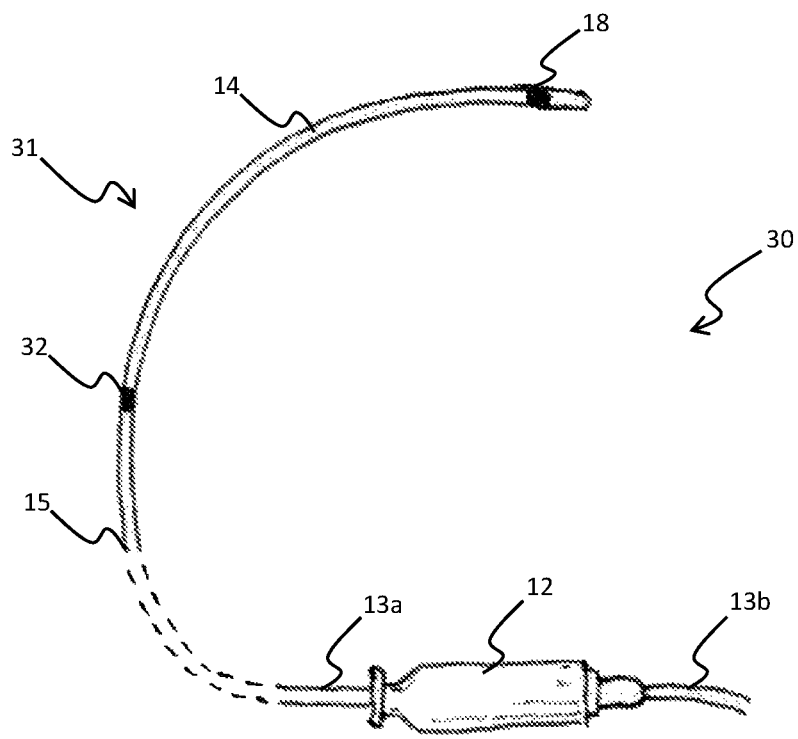
FIG. 4 is a top view of components of an apparatus according to a further embodiment of the present disclosure.

FIG. 4 shows another embodiment of an apparatus 30 similar to that shown in FIG. 1, and like features have been indicated with like reference numerals. In the apparatus 30, indwelling probe 31 further comprises a second three-axis accelerometer 32, also referred hereinafter as a "proximal accelerometer" 32, that is located proximally of the distal accelerometer 18. The proximal accelerometer 32 is spaced from the distal accelerometer 18 and located towards the proximal end 15 of the elongate body 14. The proximal accelerometer 32 may be provided as a motion reference. In some embodiments, the accelerometers 18, 32 are spaced at a distance between 3.5 and 6.5 cm, although other spacing may be used, e.g., depending on anatomical variation between individuals. In one embodiment, for example, the accelerometers 18, 32 are spaced at a distance of approximately 5.5 cm. The indwelling probe 31 of FIG. 4 is positioned for use in the same manner as that discussed above with respect to the indwelling probe 11 of FIG. 1. When positioned for use, the proximal accelerometer 32 is located in proximity to the coronary sinus ostium.

In a variation of any of the above embodiments, the apparatus can further comprise one or more additional reference sensors that are coupled to the processor. The one or more sensors may include one or more external sensors such as skin surface electrodes, transthoracic ultrasound probe, transoesophageal ultrasound probe, radiofrequency patch, induction coil, or the like. The one or more sensors may be used as a substitute or in addition to any internal electrodes disposed on the indwelling probe.

As indicated above a processor is provided that communicates with the accelerometer(s) and optionally the electrodes and external sensors to receive data therefrom, processes the received data, and optionally stores the processed data in memory. In general, it will be recognised that any processer that is used in the present disclosure may comprise a number of control or processing modules for controlling one or more features of the present disclosure and may also include one or more storage elements, for storing desired data, e.g., raw or processed acceleration data. The modules and storage elements can be implemented using one or more processing devices and one or more data storage units, which modules and/or storage elements may be at one location or distributed across multiple locations and interconnected by one or more communication links. Processing devices may include computer systems such as desktop computers, laptop computers, tablets, smartphones, personal digital assistants and other types of devices, including devices manufactured specifically for the purpose of carrying out methods according to the present disclosure.

Further, the processing modules can be implemented by a computer program or program code comprising program instructions. The computer program instructions can include source code, object code, machine code or any other stored data that is operable to cause the processor to perform the steps described. The computer program can be written in any form of programming language, including compiled or interpreted languages and can be deployed in any form, including as a stand-alone program or as a module, component, subroutine or other unit suitable for use in a computing environment. The data storage device(s) may include suitable computer readable media such as volatile (e.g., RAM) and/or non-volatile (e.g., ROM, disk) memory or otherwise.

The present disclosure recognises that movement of the cardiac wall generates corresponding movement of the wall of the coronary sinus. This in turn causes motion of the indwelling probe due to the probe being located within the coronary sinus. Motion of the indwelling probe can be detected by the accelerometer(s) on the indwelling probe to determine cardiac wall movement. Moreover, changes to the cardiac wall movement over time can be detected.

Figure 5:
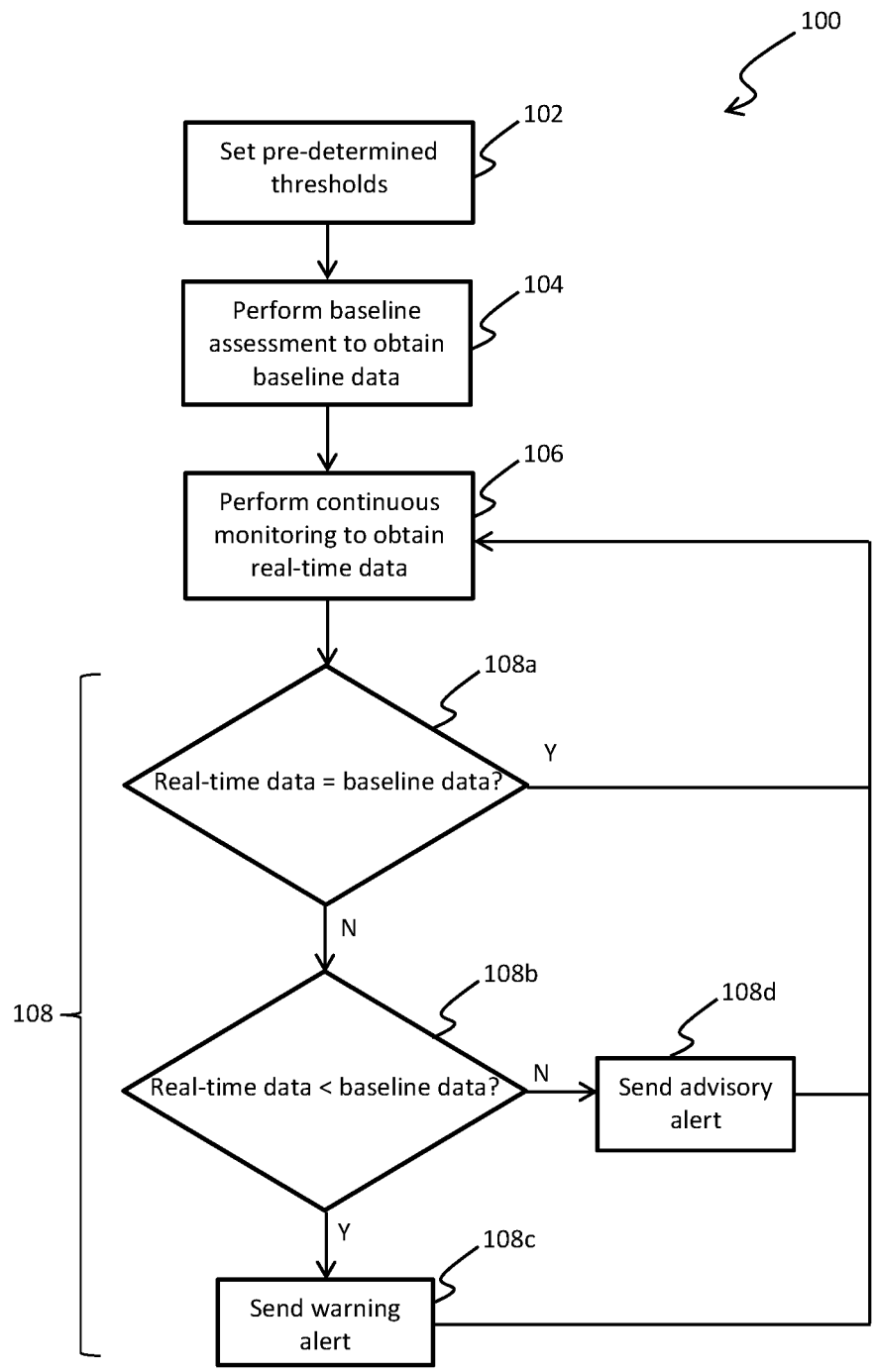
FIG. 5 is a flow diagram showing an example method of monitoring cardiac dysfunction.

FIG. 5 shows an example method 100 of monitoring cardiac dysfunction using the apparatus according to any one of the embodiments described above, which can be carried by a processor in conjunction with a memory. The method 100 comprises setting pre-defined thresholds 102, performing baseline assessment 104, performing continuous real-time monitoring 106, and comparing baseline data with real-time data 108.

(1) Set Pre-Defined Thresholds

As indicated, at 102 of the method 100, pre-defined thresholds are set. Specifically, in this embodiment, pre-defined threshold levels for volumetric displacement of the indwelling probe and cardiac wall deformation are set and stored in memory.

In some embodiments, the predefined threshold level for the volumetric displacement may be expressed as a percentage change in volume, which percentage change may be from 5 to 20%, for example. The pre-defined threshold level may provide a reference level for the purposes of triggering an alert if volumetric displacement and/or cardiac wall deformation falls below the reference level. Additionally or alternatively, pre-defined threshold levels for linear displacement of the indwelling probe and cardiac wall deformation can be set and stored in a memory. The threshold levels may also be applied to movement in one or more individual X, Y and Z axes of the accelerometer. In some embodiments, the threshold levels may be varied by a clinician to reduce or eliminate the occurrence of false alarms.

In some embodiments, the user/operator is prompted by an interface such as a software interface to enter an upper limit and lower limit threshold for displacement of the indwelling probe and cardiac wall deformation, such as the volumetric or linear displacement. These limits may be stored in memory and retrieved for subsequent procedures. In some embodiments, the thresholds may be pre-determined from clinical trials and may be representative of an average upper limit and an average lower limit of cardiac motion/wall displacement derived from a group of healthy subjects. Additionally or alternative, in some embodiments, the thresholds may be pre-determined from a technique such as cardiac 4D magnetic resonance imaging, cardiac CT imaging, or echocardiographic imaging.

(2) Perform Baseline Assessment

As indicated, at 104 of the method 100, a baseline assessment is performed using the apparatus according to any one of the embodiments described above. For example, once the indwelling probe 10, 20, 30 has been positioned in the desired location in the manner described above, a baseline assessment is performed so as to generate baseline data for volumetric displacement and/or cardiac wall deformation. Baseline data is used as a reference with which real-time volumetric displacement and/or cardiac wall deformation data is to be compared. Real-time volumetric displacement and/or cardiac wall deformation data that differs from baseline data can trigger one or more alerts, as will be discussed later.

An example process of performing baseline assessment is now described. In some embodiments, the process may be commenced only when clinical parameters are deemed stable, e.g., as assessed by the clinician. The clinical parameters can include patient position or body movement, patient respiration, operating table orientation, blood volume, electrolyte balance, arterial or venous irrigation, anaesthetic agents or otherwise.

Acceleration data detected by the accelerometer(s) from the displacement of the indwelling probe 10, 20, 30, due to normal cardiac motion, and data from other incorporated sensors, is recorded during an epoch of predetermined time or consecutive series of cardiac cycles (e.g., 10 heart beats) and stored in memory. The epoch may be a few seconds, such as from 5 to 8 seconds, although other time periods are possible.

The acceleration data may be recorded as acceleration data for each of the three different axes of the accelerometer.

Optionally, the acceleration data may be filtered to remove signal artefact. The signal artefact may arise from respiration movement, cardiac ectopy, patient movement, or combinations thereof. Signal artefact caused by respiration movement may be removed using high-pass or band-pass filtering of the acceleration data. The present disclosure recognises that high-pass filtering with a cut-off frequency of 0.12-0.15 Hz can be effective in eliminating artefact arising from respiration movement in the range of 8 to 30 breaths per minute. The present disclosure also recognises that statistical removal of outlier data may be effective in removing artefactual information occurring during a surgical procedure, such as cardiac ectopy or patient movement.

The processor then performs a first calculation to determine displacement data based on the recorded acceleration data. In a preferred embodiment, the first calculation is double integration.

The displacement data is then further processed to derive volumetric displacement data of the indwelling probe. Volumetric displacement data is calculated for each X, Y and Z axis of the accelerometer(s). Both the mean value and standard deviation of the volumetric displacement data for each X, Y and Z axis are calculated and compared. If the calculated standard deviation is greater than 10% of the mean value for any X, Y and Z axis, then baseline assessment is repeated. If the calculated standard deviation is less than 10% of the mean value, then the mean volumetric displacement data for each X, Y and Z axis is stored in memory.

In this or alternative embodiments, if the calculated standard deviation is less than 10% of the mean value, then a three-dimensional (3D) point-cloud of the temporal volumetric displacement data is stored in memory. Optionally, the volume of the displacement point-cloud may be calculated. To achieve this, a tessellated surface of the irregular point cloud is first computed. The tessellated surface and point-cloud volume may be calculated by, for example, convex hull using Qhull software. It is envisaged that other techniques may be utilised for the calculation of the tessellated surface and point-cloud volume. Although the above comparison of standard deviation and mean value of the volumetric displacement data has been made with reference to a 10% standard deviation threshold, it will be appreciated that the standard deviation threshold may be varied depending on the level of sensitivity required. For example, a standard deviation threshold of 5% may be utilised for increased sensitivity, or a standard deviation threshold of 15% may be utilised for less sensitivity.

In this or in alternative embodiments, if the mean displacement±error for an epoch is not statistically within the pre-determined threshold limits as determined at 102, an advisory message or alarm warning is issued to indicate abnormal cardiac motion, unstable-clinical parameters, and/or to indication to repeat baseline assessment 104 to obtain data over a different epoch. If the mean displacement±error is within the pre-determined threshold range (reference values) or the operator wishes to override the alarm warning or advisory message, the displacement data recorded during the epoch is stored in memory as baseline data, and the continuous real-time monitoring 106 performed. The mean displacement and the associated error (e.g., standard deviation, variance, or standard error), can be calculated from the range of displacement data observed during the epoch.

Baseline assessment of cardiac wall deformation may also be performed using the indwelling probe 30. For example, regional cardiac wall deformation between two sites of the heart, that are within proximity of the distal and proximal accelerometers, may be calculated at any time-point of the cardiac cycle as the difference in displacement between the accelerometer pairs. The maximum range of regional deformation within a given cardiac cycle can be calculated by subtracting the maximum deformation observed over a given cardiac cycle from the minimum deformation observed over that cycle. For this example, cardiac wall deformation may be measured between the coronary ostium and the postero-lateral to lateral aspect of the atrioventricular groove of the heart (near to the valve of Vieussens).

(3) Perform Continuous Real-Time Monitoring

As indicated, at 106 of the method 100, continuous real-time monitoring is performed. The approach to continuous real-time monitoring can vary for the apparatus according to different embodiments described above.

Figure 6:
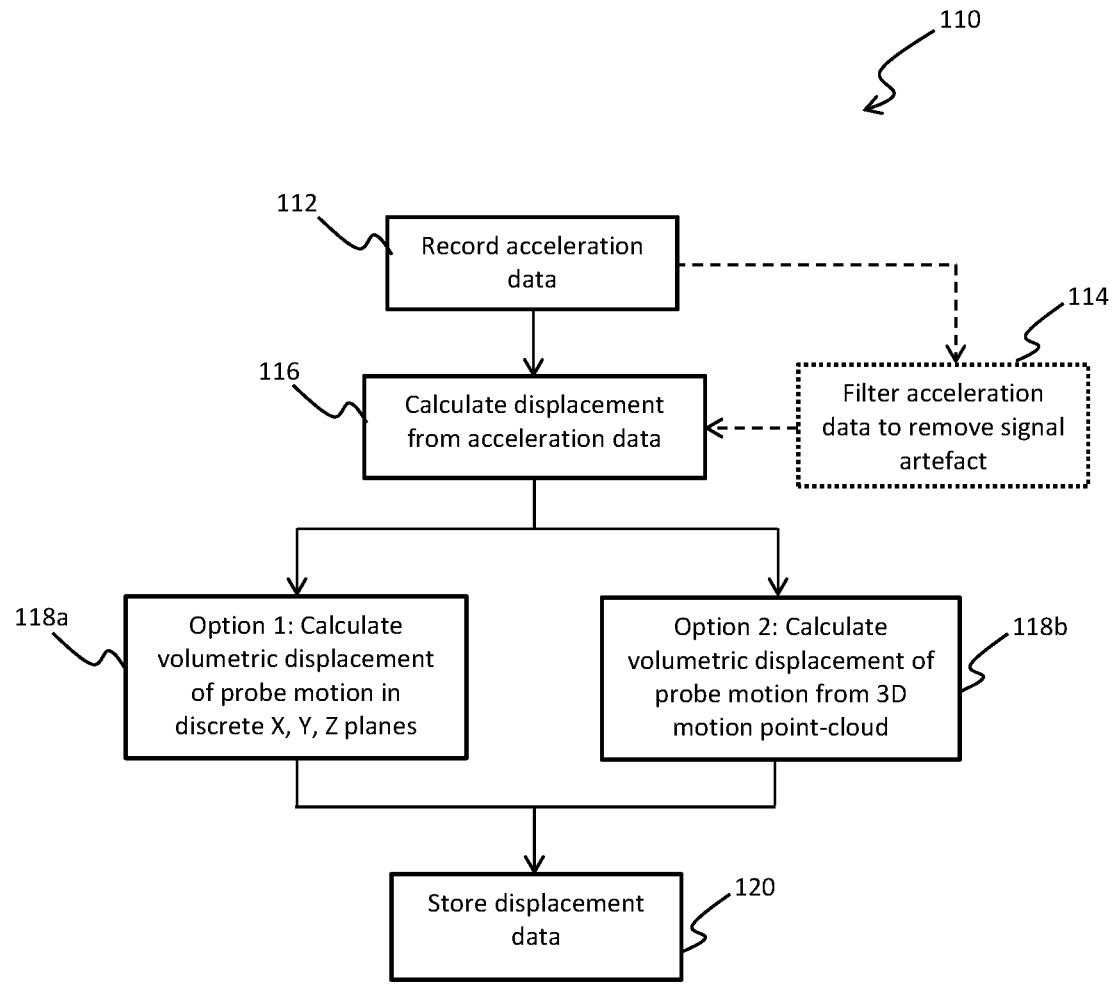
FIG. 6 is a flow diagram showing a process of continuous real-time monitoring of cardiac activity using the apparatus of FIG. 1.

With reference to the embodiment of FIG. 1 described above, and with further reference to FIG. 6, continuous real-time monitoring of cardiac activity can be performed using the apparatus 10, which comprises the indwelling probe 11 with the single distal accelerometer 18. The processor of the apparatus 10 can carry out a method 110 as follows.

At step 112, acceleration data detected by the distal accelerometer 18 from the displacement of the indwelling probe 11 is recorded over a first time period and stored in memory. The first time period may range from 5 to 8 seconds, for example.

Optionally, at step 114, acceleration data may be filtered to remove signal artefact. The signal artefact may arise from respiration movement, cardiac ectopy, patient movement, or combinations thereof. Signal artefact caused by respiration movement may be removed using high-pass or band-pass filtering of acceleration data. The present disclosure recognises that high-pass filtering with a cut-off frequency of 0.12-0.15 Hz can be effective in eliminating artefact arising from respiration movement in the range of 8 to 30 breaths per minute. The present disclosure also recognises that statistical removal of outlier data may be effective in removing artefactual information occurring during a surgical procedure, such as cardiac ectopy or patient movement.

At step 116, the processor performs a first calculation to determine displacement data based on the recorded acceleration data. In a preferred embodiment, the first calculation is double integration.

The displacement data is then further processed to derive volumetric displacement data of the indwelling probe 11.

At step 118a, volumetric displacement data is calculated in discrete X, Y and Z axes of the accelerometer 18. Advantageously, such a calculation can be performed using simple and low-tech hardware.

Alternatively, at step 118b, volumetric displacement data can be calculated from 3D motion point-cloud. The present disclosure recognises that calculating volumetric displacement from 3D motion point-cloud is a robust method to calculate 3D displacement of the heart as the resultant calculation is independent of the axial-orientation of the indwelling probe 11. The indwelling probe 11 therefore does not need to be repositioned in the same axial-plane as that for baseline assessment, so long as the indwelling probe 11 is positioned in the approximate location as that performed during baseline assessment. Further, such calculations are not affected if the patient is repositioned differently to the baseline state.

The resultant volumetric displacement data from 118a or 118b is then stored in memory at step 120. The above described steps can be repeated over subsequent time periods.

Figure 7:
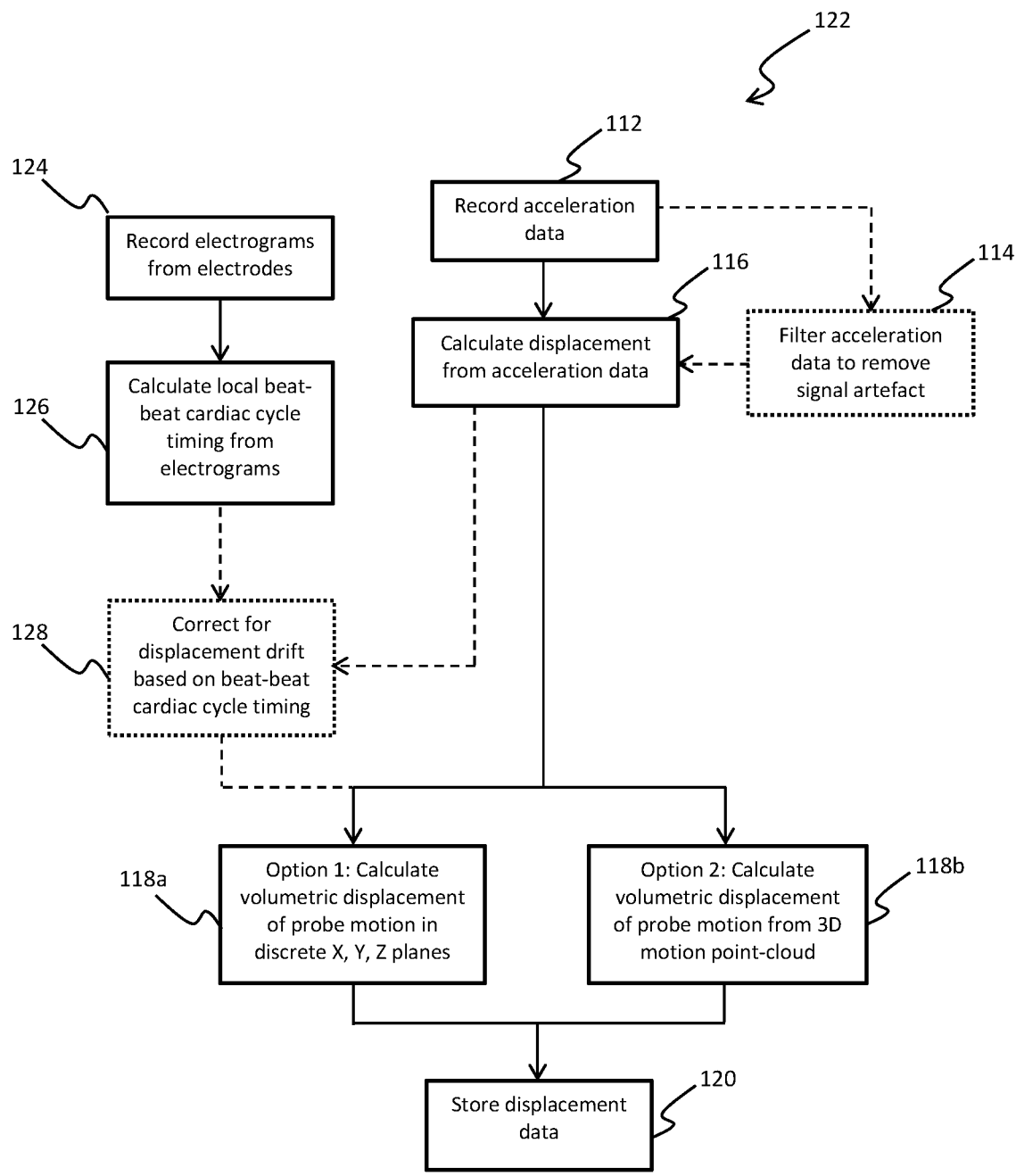
FIG. 7 is a flow diagram showing a process of continuous real-time monitoring of cardiac activity using the apparatus of FIG. 3.

With reference to the embodiment of FIG. 3 described above, and with further reference to FIG. 7, continuous real-time monitoring of cardiac activity can be performed using the apparatus 20, which comprises the indwelling probe 21 with the single distal accelerometer 18 and electrodes 22. In this embodiment, the apparatus 20 may be utilised to provide additional internal reference data as described below. The processor of the apparatus 20 can carry out a method 122 as follows. (The steps of FIG. 7 that are identical to those shown in FIG. 6 have been indicated with like reference numerals.)

At step 112, acceleration data detected by the distal accelerometer 18 from the displacement of the indwelling probe 21 is recorded over a first time period and stored in memory. The first time period may range from 5 to 8 seconds, for example.

Optionally, at step 114, the recorded acceleration data may be filtered to remove signal artefact in the same manner described above for the method 110.

At step 116, the processor performs a first calculation to determine displacement data based on the recorded acceleration data. In a preferred embodiment, the first calculation is double integration.

At step 124, electrograms detected by the electrodes 22 of the indwelling probe 21 are concurrently recorded over the first time period. The recorded electrograms may be utilised to confirm contact with the heart wall based on electrogram amplitude. Contact with the heart wall may also be confirmed by delivering a short duration electrical current (e.g. 0.1 to 25 mA at a 2 ms pulse width) from a single (unipolar) electrode or paired (bipolar) electrodes at a frequency greater than the intrinsic heart rate. The amount of current required to accelerate the intrinsic heart rate to the desired rate can be utilised as a deterministic factor of contact.

At step 126, the recorded electrograms are then utilised to calculate beat-to-beat cardiac cycle timing data.

The present disclosure recognises that the indwelling probe 21 may be subject to a degree of inherent displacement drift (displacement shift) when positioned for use in the coronary sinus 2. As such, and optionally at step 128, the beat-to-beat cardiac cycle timing data may then be applied to the displacement data obtained in step 116 to re-calibrate the positioning of the indwelling probe 21 at a particular fixed point or average point (i.e. mean centroid) in the cardiac cycle for every cardiac cycle. Such an application enables the displacement drift of the indwelling probe 21 to be corrected.

One example approach of correcting the displacement drift over a given set of cardiac cycles may include (1) assessing the average displacement of each cardiac cycle, (2) calculating the average position (i.e. mean centroid) of all cardiac cycles within the given set of cardiac cycles, and (3) normalising the displacement at a particular time point by calculating the difference between the average displacement of that cardiac cycle and the set of cardiac cycles.

At step 118a or 118b, the displacement data is further processed to derive volumetric displacement data of the probe 21 and the resultant volumetric displacement data is then stored in memory (at step 120) in the same manner described above for the method 110. The above described steps can be repeated over subsequent time periods.

Figure 8:
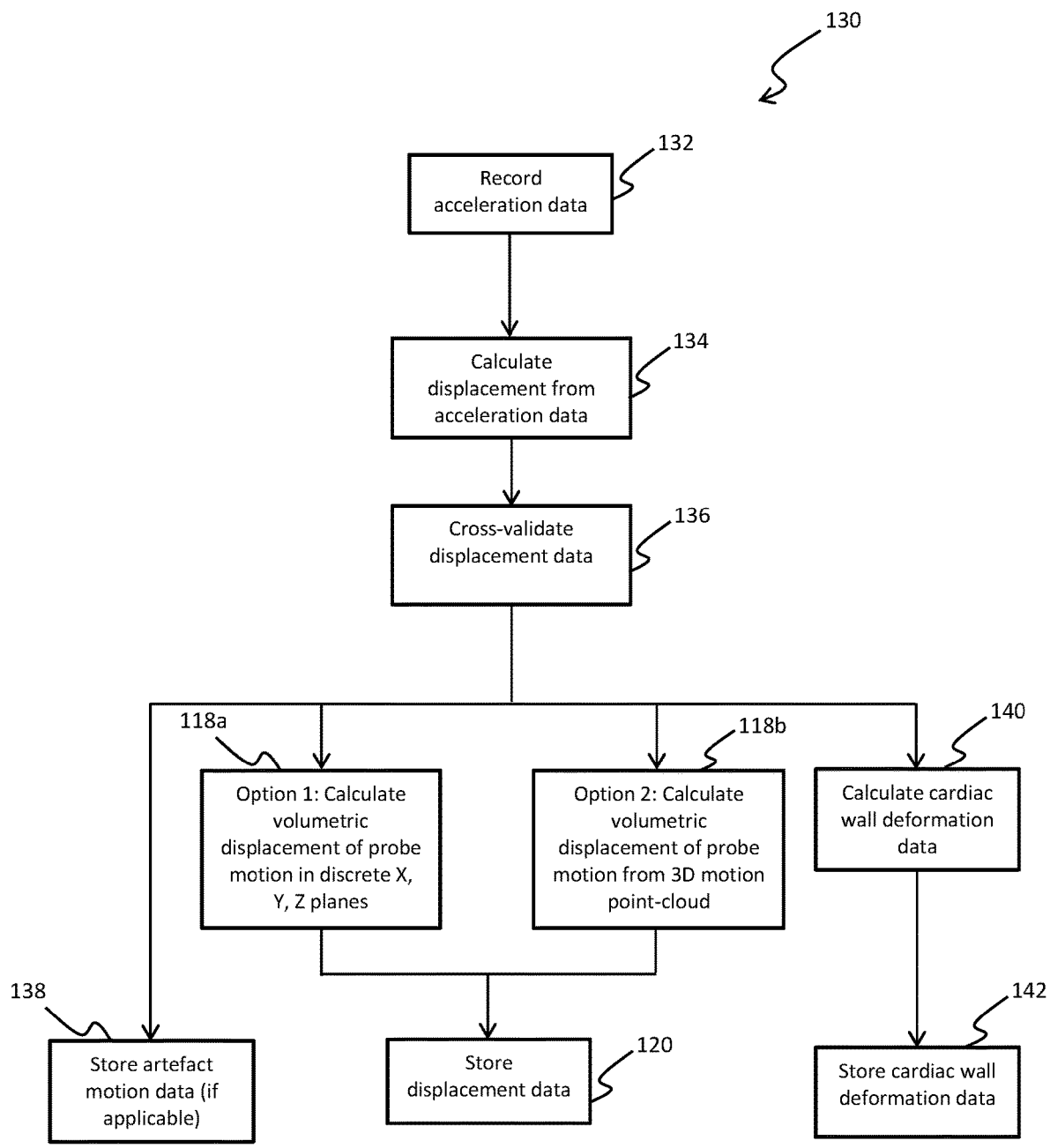
FIG. 8 is a flow diagram showing a process of continuous real-time monitoring of cardiac activity using the apparatus of FIG. 4.

With reference to the embodiment of FIG. 4 described above, and with further reference to FIG. 8, continuous real-time monitoring of cardiac activity can be performed using the apparatus 30, which comprises the indwelling probe 31 with distal and proximal accelerometers 18, 32. The processor of the apparatus 30 can carry out a method 130 as follows. (The steps of FIG. 8 that are identical to those shown in FIGS. 6 and 7 have been indicated with like reference numerals.)

At step 132, acceleration data detected by the distal and proximal accelerometers 18, 32 from the displacement of the indwelling probe 31 is recorded over a first time period. The first time period may range from 5 to 8 seconds, for example.

At step 134, the processor performs a first calculation to determine displacement data based on the recorded acceleration data of each accelerometer 18, 32. In a preferred embodiment, the first calculation is a double integration.

At step 136, the displacement data of each accelerometer is then cross-validated to differentiate artefact motion data from valid displacement data of the indwelling probe. Artefact motion data may arise from, for example, respiration, cardiac ectopy or whole-body motion. Due to the spacing of the accelerometers 18, 32 on the indwelling probe 31, motion resulting in similar or dissimilar motion between both accelerometers 18, 32 in the plane of the atrioventricular groove of the heart can be identified. The present disclosure recognises that respiratory motion results in similar motion in both accelerometers 18, 32 due to whole heart movement in the plane of the atrioventricular groove. Such movement may be utilised for example to differentiate between respiratory motion (artefact motion) and cardiac cycle motion, which results in dissimilar motion between both accelerometers 18, 32. Any detected artefact motion from the cross-validation is then stored in memory at step 138.

The validated displacement data is further processed to derive volumetric displacement data of the probe 31 (at step 118a or 118b) and the resultant volumetric displacement data is then stored in memory (at step 120) in the same manner described above for the methods 110, 122.

Alternatively, at step 140, more specific cardiac wall deformation data can be calculated based on the validated displacement data. This involves calculating Cartesian (i.e. straight line) distance of displacement data between accelerometer pairs. In this particular embodiment, the Cartesian distance between the distal and proximal accelerometers 18, 32 can be calculated. It will be appreciated however that additional accelerometers may be provided in the indwelling probe 31 and any combination of accelerometers can be used to calculate a Cartesian distance. The Cartesian distance provides a measure of cardiac wall deformation between two or more sites along the indwelling probe 31 at a discrete time-point. The cardiac wall deformation data from 140 is then stored in memory at step 142. The above described method can be repeated over subsequent time periods.

Figure 9:
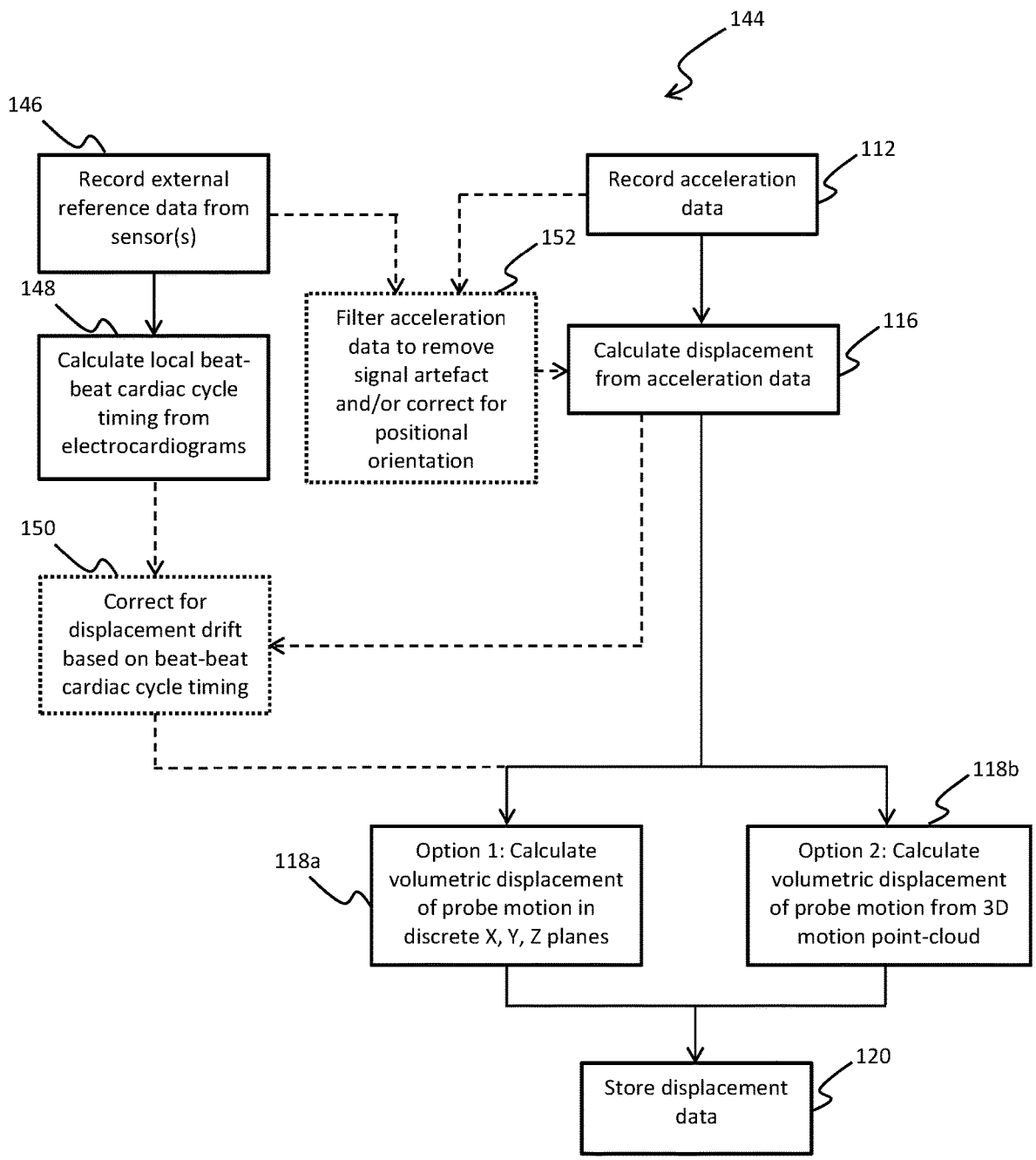
FIG. 9 is a flow diagram showing a process of continuous real-time monitoring of cardiac activity using an apparatus according to another embodiment of the present disclosure.

With reference to FIG. 9, continuous real-time monitoring of cardiac activity using an apparatus having an indwelling probe with a single distal accelerometer and additional sensors, e.g. external sensors, is now described. The processor of the apparatus can carry out a method 144 as follows. (The steps of FIG. 9 that are identical to those shown in FIGS. 6, 7 and 8 have been indicated with like reference numerals.)

At step 112, acceleration data detected by the distal accelerometer from the displacement of the indwelling probe is recorded over a first time period and stored in memory. The first time period may range from 5 to 8 seconds, for example.

At step 116, the processor performs a first calculation to determine displacement data based on the recorded acceleration data. In a preferred embodiment, the first calculation is a double integration.

At step 146, reference data from the one or more additional sensors are recorded. The reference data provides additional information which may be utilised for correcting displacement drift of the indwelling probe, correcting positional mis-orientation of the indwelling probe, removing signal artefact and/or providing additional diagnostic information regarding cardiac function. In some embodiments, the additional reference data may be external reference data and may include, but is not limited to, electrocardiograms from one or more skin surface electrodes, echocardiograms from transthoracic and/or transoesophageal ultrasound probes, bio-impedance data from radiofrequency/bio-impedance skin patches, x-ray fluoroscopy data, temperature information from one or more thermocouples or thermistors, magnetic field information from one or more magnetometers, and induction coil data.

In the embodiment depicted in FIG. 9, electrocardiograms from the skin surface electrodes of the apparatus, for example, may concurrently be recorded over the first time period.

At step 148, the recorded electrocardiograms may then be utilised to calculate beat-to-beat cardiac cycle timing data.

Optionally, at step 150, the beat-to-beat cardiac cycle timing data may be applied to the displacement data obtained in step 116 to re-calibrate the positioning of the indwelling probe at a particular fixed point in the cardiac cycle so as to account for displacement drift of the indwelling probe, in the manner described above for the method 122.

Optionally, at step 152, recorded acceleration data may be filtered to remove signal artefact in the manner described above in the method 110. Alternatively, in some embodiments, filtering of signal artefact may be performed on the calculated displacement data, rather than the recorded acceleration data. Additionally, or optionally, the additional reference data may be applied to the recorded acceleration data to assess and correct the positional orientation of the indwelling probe, and to further remove signal artefact due to respiration movement. The present disclosure recognises that with respiration movement, the heart moves cranially or caudally with respiration movement typically over a period of a few seconds, while heart motion is essentially cyclic over a period of a few hundred milliseconds. Such reference data may be utilised to adjust for respiration movement. In this regard, the present disclosure also recognises that as the heart rate can vary, reference data must also be acquired simultaneously with acceleration data so as to allow for proper comparison.

The displacement data is further processed to derive volumetric displacement data of the probe (at steps 118a or 118b) and the resultant volumetric displacement data is then stored in memory (at step 120) in the same manner described above for the methods 110, 122, 130. The above described steps can be repeated over subsequent time periods.

(4) Compare Baseline Data with Real-Time Data

As indicated, at 108 of the method 100, a comparison of baseline data with real-time data is performed.

Specifically, after each time period, a comparison is made between baseline data and real-time data to monitor for cardiac dysfunction, as illustrated in FIG. 5. Hereinafter, references to "baseline data" is intended to encompass both baseline volumetric displacement data and baseline cardiac wall deformation data, and references to "real-time data" is intended to encompass both real-time volumetric displacement data and real-time cardiac wall deformation data.

If, at step 108a, real-time data is the same as baseline data, cardiac wall motion is deemed normal and continuous real-time monitoring is repeated over a subsequent time period.

If, at step 108a, real-time data is different to baseline data, cardiac wall motion is deemed abnormal and a determination is made on the severity and nature of cardiac dysfunction.

At step 108b, a comparison is made on whether real-time data is less than or greater than baseline data. If real-time data is less than baseline data, the processor generates a warning alert indicative of impaired/inhibited cardiac wall motion, and outputs the alert at step 108c. Impaired cardiac wall motion may arise from pericardial effusion, cardiac tamponade, electromechanical dissociation, increased cardiac blood volume pressure due to ablation procedures, or combinations thereof.

If, at step 108b, real-time data is greater than baseline data, the processor generates an advisory alert indicative of excessive cardiac wall motion, and outputs the alert at step 108d. Excessive cardiac wall motion may arise from tachycardia, increased cardiac contractility, unstable probe positioning, steam pop, cardiac ectopy, a potential defibrillation event, or combinations thereof.

It is envisaged that the steps of performing real-time monitoring and comparing real-time data with baseline data discussed above will be continuously performed over subsequent time periods.

EXAMPLE

Figure 10:
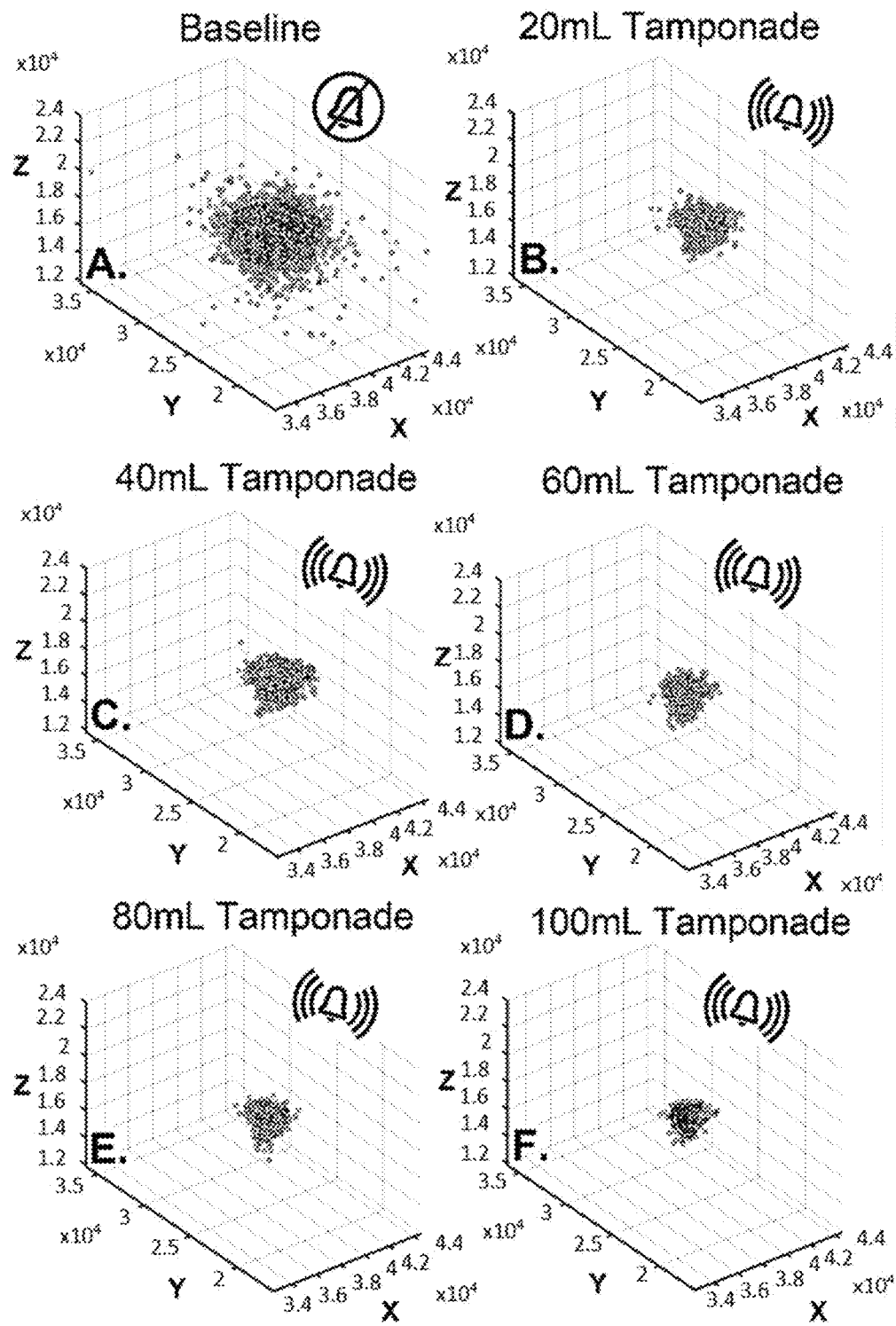
FIG. 10A is a plot illustrating baseline volumetric displacement data.
FIG. 10B to 10F are plots illustrating volumetric displacement data responsive to incremental in vivo simulation of cardiac tamponade by intrapericardial injection of 20-100 mL of 0.9% saline solution (normal saline)
FIG. 10G is graph illustrating total volumetric displacement data responsive to incremental in vivo simulation of cardiac tamponade by intrapericardial injection of 20-100 mL of 0.9% saline solution (normal saline)
FIGS. 10H to 10J are graphs illustrating volumetric displacement data in singular dimensions X, Y and Z, respectively, responsive to incremental in vivo simulation of cardiac tamponade by intrapericardial injection of 20-100 mL of 0.9% saline solution (normal saline).

FIGS. 10A to 10J show example displacement data recorded during in vivo simulation of cardiac tamponade using an indwelling probe with a distally located accelerometer implanted in the coronary sinus. FIG. 10A shows a plot of baseline volumetric displacement data indicating safe limits, with which volumetric displacement data of the probe is to be compared. In this example, cardiac tamponade is simulated through the injection of bolus saline solution, in 20 mL increments (to a total of 100 mL) over a 20 minute period, into the pericardial space. Calculated volumetric displacement data across the X, Y and Z axes based on variations in acceleration data detected by the accelerometer are shown in FIGS. 10B to 10J. An alert signal is indicated due to inhibition of cardiac wall motion above a set predefined threshold level. The horizontal dotted line of FIGS. 10G to 10J represents the set pre-defined threshold level for the purposes of triggering an alert.

The example indicates that simulated tamponade conditions results in significant attenuation of displacement data. These effects were observed even when a small volume of saline (20 mL) was injected into the pericardial space (FIG. 10B). The example also indicates that additional bolus injections of saline into the pericardial space (FIGS. 10C to 10F) did not significantly attenuate displacement data above what was observed for the initial simulated dose (FIG. 10B). This highlights the importance of constant monitoring (involving signalling of an alert) of cardiac wall motion during tamponade. Such monitoring can be achieved through the implementation of embodiments of the present disclosure.

Whilst in embodiments described above, the indwelling probe is positioned within the coronary sinus, in other embodiments, the indwelling probe may be deployed in a chamber of the heart or other coronary vessel. Further, in some embodiments, the accelerometer may be located elsewhere on the elongate body of the indwelling probe aside from being at or adjacent the distal tip.

In a further application of the embodiments of the present disclosure, the indwelling probe may also comprise an ablation tip so as to provide ablation therapy to a patient. The indwelling probe may be similar to that shown in any one of FIG. 1, 3 or 4 with the addition of the ablation tip at the distal end of the indwelling probe.

Figure 11:
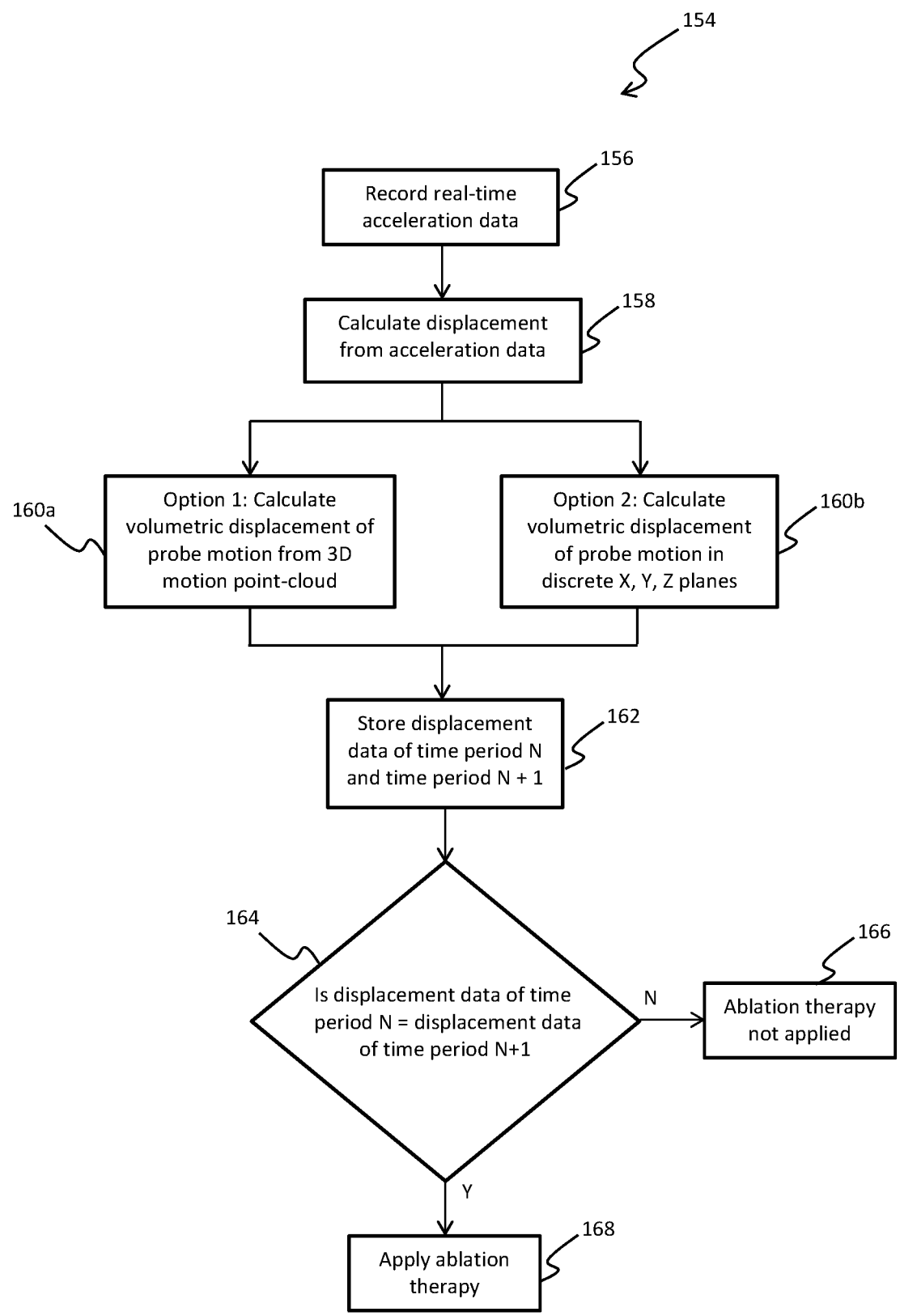
FIG. 11 is a flow diagram showing a process of continuous real-time monitoring of probe displacement using an apparatus according to a further embodiment of the present disclosure, wherein the probe includes an ablation tip.

The motion of the indwelling probe is continuously monitored via the distal accelerometer to determine whether ablation therapy may be effectively applied to the intended therapy site. An example process of continuous real-time monitoring of indwelling probe motion is now described with reference to FIG. 11. The processor of the apparatus can carry out a method 154 as follows.

At step 156, acceleration data detected by the distal accelerometer from the displacement of the indwelling probe is recorded over a first time period and stored in memory.

At step 158, the processor performs a first calculation to determine displacement data based on the recorded acceleration data of the first time period. In a preferred embodiment, the first calculation is double integration.

The displacement data of the first time period is then further processed to derive volumetric displacement data of the indwelling probe. At step 160*a*, volumetric displacement data can be calculated from 3D motion point-cloud in the same manner described above for the methods 110, 122, 130 and 144.

Alternatively, at step 160*b*, volumetric displacement data may be calculated in discrete X, Y and Z axes of the accelerometer in the same manner described above for the methods 110, 122, 130 and 144.

The resultant volumetric displacement data of the first time period from 160*a* or 160*b* is then stored in memory at step 162.

The above described steps are repeated over a second time period, and the resultant volumetric displacement data of the second time period is also stored in memory at step 162.

At step 164, a comparison is made between the volumetric displacement data of the first time period and the volumetric displacement data of the second time period. If the volumetric displacement data of the first and second time periods are different, the indwelling probe is deemed unstable. For example, this may be due to unstable positioning of the probe or displacement drift of the probe from the intended therapy site. In this instance, at step 166, ablation therapy can either not be applied due to unstable positioning or ablation energy can be increased to account for displacement drift of the indwelling probe from the therapy site.

If, at step 164, the volumetric displacement data of the first and second time periods are the same, the indwelling probe is deemed stable. Ablation therapy can then be applied normally at step 168.

The embodiments described above can have numerous advantages. For example, they may allow higher sensitivity to early changes in cardiac contractility by providing real-time monitoring of cardiac wall motion. Moreover, they may be utilised proactively rather than reactively to acute cardiac dysfunction during, for example, pericardial effusion, cardiac tamponade, electromechanical dissociation or increased cardiac blood volume pressure. This may also add no additional complexity to clinical procedures. Further, the embodiments may provide quantitative monitoring of cardiac contractile force which may be exerted in the event of cardiac defibrillation. This may be useful in determining the optimal power (in joules) and electrode positioning vector of the defibrillator generator. The embodiments may also allow for monitoring of steam pop associated with radiofrequency ablation performed from the probe tip.

It will be appreciated by persons skilled in the art that numerous variations and/or modifications may be made to the above-described embodiments, without departing from the broad general scope of the present disclosure. As one example, according to embodiment of the present disclosure, rather than performing a first calculation (e.g. double integration) to determine a first displacement data from recorded acceleration data, the method may instead comprise performing a first calculation (e.g. single integration) to determine a first velocity data from the recorded acceleration data. In these embodiments, it is envisaged that cardiac dysfunction may also be monitored based on the first velocity data derived from single integration of the acceleration data. The present embodiments are, therefore, to be considered in all respects as illustrative and not restrictive.

The invention claimed is:

1. A method of monitoring for pericardial effusion or cardiac tamponade in a patient, the method comprising:
   inserting a probe within a coronary sinus of the patient, wherein the probe comprises a motion sensor configured to sense motion of the probe based on movement of a wall of the coronary sinus;
   obtaining sensed data indicative of movement of the wall of the coronary sinus from the probe; and
   processing the sensed data, using a processor coupled to the probe for receiving sensed data from the probe, to monitor for pericardial effusion or cardiac tamponade, wherein the processing comprises:
      determining volumetric displacement data based on the sensed data,
      comparing the volumetric displacement data with baseline volumetric displacement data,
      monitoring for a reduction in volumetric displacement based on the comparison, and
      triggering an alert indicative of pericardial effusion or cardiac tamponade upon the volumetric displacement falling below a pre-defined volumetric displacement threshold level.

2. The method of claim 1, wherein the sensed data is acceleration data.

3. The method of claim 2, wherein the probe comprises a three-axis accelerometer and the acceleration data is obtained from the three-axis accelerometer coupled to the probe.

4. The method of claim 2, wherein determining volumetric displacement data comprises performing a first calculation to determine first displacement data from the acceleration data and performing a second calculation to determine the volumetric displacement data of the probe from the first displacement data.

5. The method of claim 2, further comprising recording electrograms from at least one electrode coupled to the probe.

6. The method of claim 5, further comprising calculating beat-to-beat cardiac cycle timing data from the electrograms.

7. The method of claim 6, wherein deriving the volumetric displacement data comprises performing a first calculation to determine first displacement data from the acceleration data, and
wherein the method further comprises correcting the first displacement data using the beat-to-beat cardiac cycle timing data to account for displacement drift of the probe.

8. The method of claim 2, further comprising recording additional reference data from one or more sensors.

9. The method of claim 1, further comprising filtering the recorded acceleration data to remove signal artefact.

10. The method of claim 9, wherein the signal artefact comprises one or more of respiration movement, cardiac ectopy, and patient movement.

11. The method of claim 1, wherein the monitoring of an indication of impaired cardiac wall motion comprises generating an alert indicative of impaired cardiac wall motion based on the comparison.

12. An apparatus for monitoring for pericardial effusion or cardiac tamponade in a patient, the apparatus comprising:
an indwelling probe comprising:
an elongate body adapted for insertion within a coronary sinus of a patient, wherein the probe comprises a motion sensor configured to sense motion of the probe based on movement of a wall of the coronary sinus; and
a processor configured to monitor for pericardial effusion or cardiac tamponade, the processor being coupled to the probe for receiving sensed data from the probe that is indicative of movement of the wall of the coronary sinus and processing said sensed data, said processing comprising:
determining volumetric displacement data based on the sensed data;
comparing the volumetric displacement data with baseline volumetric displacement data;
monitoring for a reduction in volumetric displacement based on the comparison, and
triggering an alert indicative of pericardial effusion or cardiac tamponade upon the volumetric displacement falling below a pre-defined volumetric displacement threshold level.

13. The apparatus of claim 12, wherein the probe comprises a three-axis accelerometer located at or adjacent a distal end of the elongate body that senses the movement of the wall of the coronary sinus.

14. The apparatus of claim 12, further comprising two or more three-axis accelerometers spaced longitudinally along the elongate body that sense the movement of the wall of the coronary sinus.

15. The apparatus of claim 12, wherein the probe further comprises at least one electrode disposed on the external surface of the elongate body, the at least one electrode being configured to detect electrograms from cardiac activity.

16. The apparatus of claim 15, wherein the at least one electrode comprises two or more electrodes spaced longitudinally along the elongate body.

17. The apparatus of claim 12, further comprising one or more sensors coupled to the processor, the one or more sensors being configured to provide additional reference data.

18. The apparatus of claim 12, wherein the monitoring of an indication of impaired cardiac wall motion comprises generating an alert indicative of impaired cardiac wall motion based on the comparison.

* * * * *